United States Patent
Wanderstok et al.

(10) Patent No.: US 7,096,069 B2
(45) Date of Patent: Aug. 22, 2006

(54) SYSTEM FOR COLLECTING ELECTRIC WAVES FOR THE RECEPTION OF MAGNETIC INDUCTION SIGNALS EMITTED BY AN IMPLANTED ACTIVE MEDICAL DEVICE

(75) Inventors: Georges Wanderstok, Clamart (FR); Vincent Tanche, Gometz le Chatel (FR)

(73) Assignee: ELA Medical S.A.S., Montrouge (FR)

( * ) Notice: Subject to any disclaimer, the term of this patent is extended or adjusted under 35 U.S.C. 154(b) by 251 days.

(21) Appl. No.: 10/857,350

(22) Filed: May 28, 2004

(65) Prior Publication Data

US 2005/0010268 A1 Jan. 13, 2005

(30) Foreign Application Priority Data

May 28, 2003 (FR) .................................. 03 06461

(51) Int. Cl.
*H04B 5/00* (2006.01)
(52) U.S. Cl. ........................... 607/60; 607/32; 128/903
(58) Field of Classification Search .................. 607/32, 607/60, 65, 154–156; 128/903
See application file for complete search history.

(56) References Cited

U.S. PATENT DOCUMENTS

| | | | |
|---|---|---|---|
| 5,674,265 A | 10/1997 | Deschamps et al. | ........... 607/60 |
| 5,741,315 A | 4/1998 | Lee et al. | ...................... 607/60 |
| 6,298,271 B1 | 10/2001 | Weijand | ...................... 607/60 |

FOREIGN PATENT DOCUMENTS

| | | |
|---|---|---|
| EP | 0 797 317 A1 | 9/1997 |
| WO | WO 01/054467 A1 | 1/2001 |

*Primary Examiner*—Robert Pezzuto
*Assistant Examiner*—Yun Haeng Lee
(74) *Attorney, Agent, or Firm*—Orrick Herrington & Sutcliffe LLP

(57) ABSTRACT

An antenna system for collecting electric waves for the reception of magnetic induction signals emitted by an active implantable medical device. The system includes an antenna that comprises a reception coil (10) and a compensation coil (20), each of which preferably includes at least one series of turns (12, 22) wound around respective mandrels (16, 26) made out of a nonmagnetic material. The mandrels are positioned side by side with their respective axes (18, 28) spaced apart and parallel, and with their cross sections areas not superimposed. The cross section of the mandrel (26) of the compensation coil (20) is less than that of the mandrel (16) of the reception coil (10). The series of turns (22) of the compensation coil (20) can be split in a plurality of groups of turns (24) wound on the same mandrel (26), with an axial spacing and connected in series, preferably with the sections of winding and/or different numbers of turns being different. The series of turns (22) also can be distributed on separate mandrels.

11 Claims, 1 Drawing Sheet

SYSTEM FOR COLLECTING ELECTRIC WAVES FOR THE RECEPTION OF MAGNETIC INDUCTION SIGNALS EMITTED BY AN IMPLANTED ACTIVE MEDICAL DEVICE

FIELD OF THE INVENTION

The present invention relates to active implanted medical devices, and more particularly to the collection of the signals emitted at the time of communication of data between an implanted device and an external control console or programmer. The known active implanted medical devices include without limitation cardiac pacemakers, defibrillators, cardiovertors, cardiac resynchronization devices, and multisite devices, as well as neurological devices, pumps for the diffusion of medical substance, and cochlear implants.

BACKGROUND OF THE INVENTION

Once implanted, active implantable medical devices are typically programmed remotely, external to the patient, by means of a control console called a "programmer." The verification of the operating parameters of the implant or the transmission of information recorded by the implant is carried out by electromagnetic transmissions, called "telemetry" in the technique in question. This console or programmer is provided with a telemetry head that is placed over the site of the implant. The head, often called an "antenna", includes an induction coil that acts as an antenna and collects the magnetic field coming from the implanted device.

One conventional configuration usually employed provides a single antenna placed in the body of the programmer head. The induced signal collected by that antenna is then amplified, conditioned and processed to extract therefrom information communicated from the implant. This configuration, however, presents the disadvantage of receiving at the same time as the useful signal all of the surrounding radio-electric disturbances (i.e., noise), which are all the more difficult to eliminate because the band-width of the system must be large.

To increase the signal-to-noise ratio, it is disclosed in EP-A-0 661 077 and its corresponding U.S. Pat. No. 5,674,265, commonly assigned herewith to ELA Medical, to use a plurality of collecting coils and to process the collected signals using a particular linear combination, making it primarily possible to preserve the useful component of the signal and eliminate the major part of the noise components coming from parasitic sources. The improvement of the signal-to-noise ratio is indeed essential if one wishes to increase the data transmission rate and/or volume from the implant towards the programmer, for example, if one wants to download large data stored in the implant such as Holter recordings taken of an endocardial ECG over a duration of several hours representing a volume of several megabits of data.

To further improve the performance of the programmer, it is disclosed in EP-A-0 797 317 and its counterpart U.S. Pat. No. 5,741,315, also commonly assigned herewith to ELA Medical, to use a particular geometry of collecting coils, making it possible to collect signals such that the noise component is greatly reduced at the collection stage, even before any signal processing by the electronic circuits. EP 797317 and U.S. Pat. No. 5,741,315 proposes to use two distinct coils on a common magnetic circuit such as a ferrite cup, namely a reception coil and a compensation coil. The reception coil, for example, is wound on the core of the ferrite cup, while the compensation coil is wound coaxially on the periphery of the cup. In this manner, the magnetic induction field lines of the useful component cross the receiving coil only once, whereas they cross the compensation coil twice in opposed directions. On the other hand, remote parasitic inductions cross the two coils in the same direction and almost identically, which easily makes it possible to isolate the interfering signals in order to remove them from received signal and thereby leave the useful signal.

Further, WO-A-01/05467 (assigned to Medtronic) proposes to use two distinct antennas for reception, but the antennas are positioned to be concentric and coplanar. The signals resulting from the two windings are withdrawn so as to eliminate the remote disturbances, which induce identical signals that are opposite in phase. The signal emitted by the implant at short distance induces voltages of opposite phases but of different amplitudes, which are thus not cancelled and make it possible to extract from the surrounding noise a useful signal whose secondary treatment can be simplified.

With these known configurations implementing a plurality of coils, the differentiation is excellent, but to the detriment of the practical range. Indeed, the distance between the antennas is limited by the dimensions of the programmer head. An implant located more than few centimeters from the antenna is already regarded as a remote disturbance; the attenuation of the signal according to the head-implant distance increases then much more quickly than the traditional law of attenuation according to the inverse of the square of the distance of separation.

To mitigate this disadvantage, one can envisage to lay out the two antennas side by side. With this configuration, however, a "dead zone" appears in a region located between the antennas, forming a "differential well" where no signal can be received. This region overlaps with the capture surfaces of the antennas and reduces the useful surface area of reception of the head. In addition, the rejection of the signals in the dead zone varies very quickly from a spatial point of view, so that a small lateral movement of the head compared to the implant can generate a significant amplitude variation, including even an inversion of the phase of the useful signal.

OBJECTS OF SUMMARY OF THE INVENTION

It is, therefore, an object of the present invention to cure this disadvantage and the above-mentioned disadvantages of the known systems.

To this end, the present invention broadly proposes a new particular geometry for the antenna system coils, making it possible to maximize the surface area in which the communication with the implant can be established.

As will become apparent to a person of ordinary skill in the art, the particular configuration according to the invention has the following advantages: (1) Compared to a differential antenna with a ferrite cup (as described in above-mentioned EP-A-0 797 317 and U.S. Pat. No. 5,741, 315, the removal of the ferrite cup obtains advantages in terms of the volume of the detection cone, of lower price, the reduced weight, the solidity, the integration facilitation, the reliability and durability; (2) Compared to a coaxial or concentric construction, as described, for example, in above-mentioned WO-A-01/05467, the absence of reduction of range for the close signals, by preserving a good rejection of the remote disturbances; (3) Compared to a symmetrical coplanar construction, the reduction of the surface area of the differential well, and (4) The possibility of using only one amplification channel, with the difference between the reception signals and the compensation signals being achieved by windings connected in series and in opposition of phase.

Broadly then, the present invention is directed to a device of the type described by the above mentioned EP-A-0 661 077 and U.S. Pat. No. 5,674,265, which patent is incorporated herein by reference in its entirety, for the reception of signals emitted by an implanted active medical device. One such device comprises means for collecting electric waves by the reception of a magnetic induction including a useful component emitted by the implanted device and a parasitic component of external origin, these means for collecting electric waves comprising at least one reception coil and at least one compensation coil.

According to a preferred embodiment of the invention, each of the reception coil and the compensation coil includes at least one series of turns wound around respective mandrels, these mandrels being made preferably out of a non-magnetic material, and positioned side by side with their respective axes distant and parallel, and with their cross sectional areas not being concurrent, i.e., not in superposition. The cross sectional area of the mandrel for the compensation coil is selected to be smaller than the cross sectional area of the mandrel for the reception coil. It should be understood that the term cross sectional area refers to the surface area of the coil (compensation or reception, as the case may be) as defined by the area circumscribed by the windings.

Very advantageously, the series of turns of the compensation coil is split in a plurality of groups of turns wound on the same mandrel, with an axial spacing between groups and with the groups connected in series.

Preferably, the turns of the compensation coil also can be wound in a honeycomb pattern, as known in the art.

In yet another preferred embodiment, the series of turns of the compensation coil is split in a plurality of groups of turns wound on a like plurality of separate mandrels, and connected in series, the various separate mandrels also having parallel axes and being positioned at the same distance from the reception coil. When the series of turns of the compensation coil is split into various groups of turns, the different groups are preferably configured to have different inductance, which can be achieved by being wound about a different cross-sectional area, or by using different a number of turns, or some combination thereof.

BRIEF DESCRIPTION OF THE DRAWINGS

Further benefits, features and characteristics of the present invention will become apparent to a person of ordinary skill in the art in view of the following detailed description of preferred embodiments of the present invention, made with reference to the annexed drawings, in which.

DETAILED DESCRIPTION OF THE INVENTION

Figure 1:
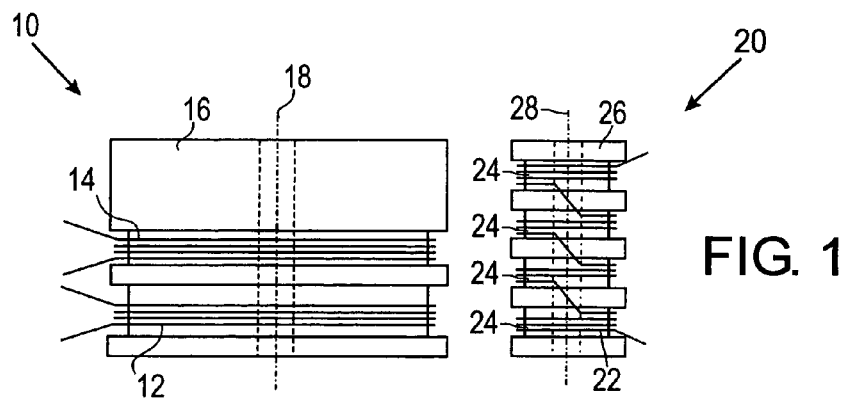
FIG. 1 is a elevation view of an antenna system according to the invention, with an emitter/receiver antenna associated with a compensation antenna.
Figure 2:
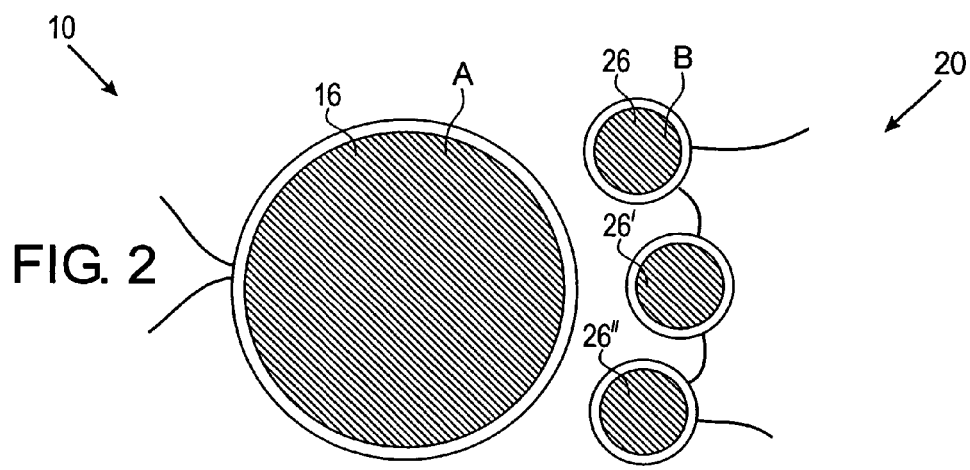
FIG. 2 is a plan view of an antenna system showing an emitter/receiver coil associated with a plurality with compensation coils.

With reference to FIGS. 1 and 2, structures of two preferred embodiments of coils for a programmer head antenna system according to the invention are shown.

It is known that, in the case of the telemetry of information coming from an implant, the useful signals as well as the interfering signals (e.g., noise and other parasitic components) are conveyed in the form of magnetic fields, and the total signal received by an antenna can be separated into a useful signal and an interfering signal. As discussed in EP-A-0 661 077 and U.S. Pat. No. 5,674,265 mentioned above, it is possible to extract from the total signal the useful component of the signal by a particular linear combination of the signals delivered by a plurality of distinct collecting coils, each receiving an induced magnetic flux and producing corresponding voltages applied to respective amplifiers whose outputs are combined in a summing stage.

The present invention proposes a particular geometry for these coils, illustrated on FIGS. 1 and 2. The antenna system of the present invention includes at least two coils, as in the embodiment illustrated in FIG. 1, namely an emitter/receiver coil 10 primarily intended, in its reception function, to collect the useful signal, and one or more coils known as "compensation" coils 20 intended to collect primarily a component of noise. The emitter/receiver antenna 10 includes a reception winding 12 and one emission winding 14 wound together around a common mandrel 16. Mandrel 16 is preferably a hollow mandrel, deprived of any magnetic material such as a ferrite, for example, having a cylindrical shape about an axis 18, with a cross sectional area (see FIG. 2) that is as large as possible, compatible with the physical dimensions of the head of the programmer. The surface in which the communication with the implant can be established is thus maximized.

The compensation antenna 20 includes a winding 22 wound around a mandrel 26, which is also preferably a hollow mandrel, cylindrical about an axis, but having a diameter that is smaller than that of mandrel 16 of the emitter/receiver antenna 10. Mandrel 26 is positioned collaterally with mandrel 16, with the respective axes 28, 18 of the mandrels being parallel. The reception winding 12 and the compensation winding 22 should have the same sensitivity with respect to the remote disturbances, and thus their number of turns must be inversely proportional to their surface areas.

It will be appreciated that the reception surface area B of the compensation antenna 20 is comparatively much smaller than reception surface area A of the emitter/receiver antenna 10, and the differential well or dead zone located between the two antennas is limited.

Winding 22 of compensation antenna 20 is advantageously divided into a plurality of groups of turns 24. Indeed, the compensation antenna 20 should not exceed a critical number of turns, corresponding to a maximum inductance limiting the band-width of the system electronics, to, for example, 300 KHz, and the band-width of the antennas to, for example, 100 KHz.

For that, in a first illustrated embodiment on FIG. 1, winding 22 is carried out in a plurality of groups 24 of arranged turns, which groups are coaxial but positioned remotely from one another (i.e., spaced apart) along the axis of the same mandrel 26. Advantageously, the numbers of turns of the various groups 24 are not identical, so that each group has a different resonance frequency, leading to a total peak resonance that is less than that of the compensation antenna 20. An example of winding 22 having four groups 24 is illustrated in FIG. 1.

Figure 3:
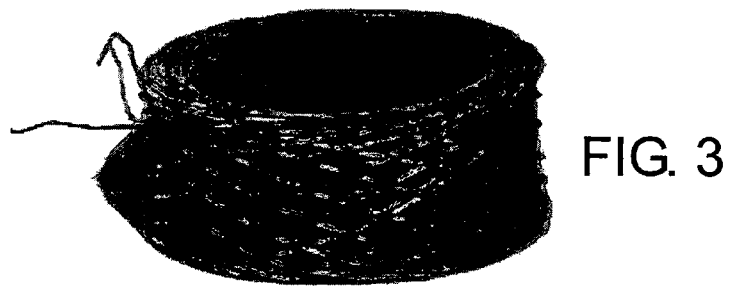
FIG. 3 is an elevated perspective view of an antenna illustrating the honeycomb pattern of windings.

In an alternative embodiment, winding 22 of compensation antenna 20 can be carried out by a technique known as a "honeycomb", i.e., with turns of windings made in a controlled over-lapping manner to produce an open-air wire-mesh with minimal points of contact between winding. An embodiment of a honeycomb winding is shown in FIG. 3.

In yet another embodiment, which may be used in the alternative or in complement, and as illustrated on FIG. 2, a plurality of groups 24 of turns of compensation antenna 20 are distributed on a like plurality of different mandrels 26, 26', 26", to give windings that are connected in series but not inductively coupled to one another. The various groups of turns 24 are positioned to be a relatively short distance, e.g., on the order of a few centimeters or less from reception antenna 10, preferably with the groups of windings in the same or approximately the same plane, to avoid the disadvantage discussed above of the coplanar antennas of equal surface areas.

The total inductance of the compensation antenna 20 is greatly reduced and its performance in terms of band-width is similarly increased. Thus, in the example of compensation antenna 20 split into three winding groups 24 of inductance L1, L2 and L3 of negligible mutual coupling, if the inductance of a not split single antenna (as illustrated FIG. 1) is equal to L, then the inductance of L1, L2 or L3 is $L/3^2=L/9$ in the case of a split antenna (illustrated on FIG. 2). The three fractions thus have together a total inductance $L'=L1+L2+L3=3 \times L/9=L/3$: the band-width is thus tripled for a given resistive load.

One of ordinary skill in the art will understand that it is possible to use for the reception simplified circuits comprising one amplification channel, the difference between the signals of reception and compensation, i.e., with a subtraction of the interfering signals of the useful signal, being able to be carried out by a simple connection of the windings of the reception antenna and of the compensation antenna in series but in opposite in phase.

Suitable devices for which the present invention has application include, for example, the 'Orchestra' branded programmer available from Ela Medical, S. A. Montrouge, France. These devices are microprocessor based telemetry systems with memory, data registers and the like (microcontrollers) having circuits for receiving, conditioning and processing detected electrical signals generated by implantable devices.

One skilled in the art will appreciate that the present invention can be practiced by other than the described embodiments, which are presented for purposes of illustration and not of limitation.

We claim:

1. A device for the reception of signals emitted by an active implanted medical device, comprising means for collecting electric waves by a reception of a magnetic induction including a useful component emitted by the implanted device and a parasitic component of external origin, said collecting means comprising at least one reception coil and at least one compensation coil;

wherein the reception coil further comprises at least one group having a first number of turns of wire wound on a first mandrel, and the compensation coil further comprises at least one group having a second number of turns of wire around a second mandrel, the first and second mandrels each having a cross section area in a plane and an axis perpendicular to said plane, and wherein said first and second mandrels are positioned side by side with their respective axes spaced apart and parallel and their cross section areas not being superimposed and wherein the cross section area of the second mandrel is smaller than the cross section area of the first mandrel.

2. The device of claim 1, wherein the at least one group of a second number of turns further comprises a plurality of groups of turns of wire wound around the second mandrel, said plurality of groups of wires being axially spaced apart along said second mandrel axis and connected in series.

3. The device of the claim 2 wherein each of said plurality of groups of turns has a different inductance.

4. The device of claim 3 wherein each of said plurality of groups of turns on said second mandrel has a different number of turns.

5. The device of claim 3 wherein each of said plurality of groups of turns around said second mandrel has a different cross sectional area.

6. The device of claim 1, wherein the at least one group of a second number of turns further comprises a plurality of groups of turns wound around a like plurality of second mandrels and connected in series, said plurality of second mandrels being positioned with respective axes in parallel and located at a first distance from the reception coil.

7. The device of the claim 6 wherein each of said plurality of groups of turns has a different inductance.

8. The device of claim 7 wherein each of said plurality of groups of turns on said second mandrels has a different number of turns.

9. The device of claim 7 wherein each of said plurality of groups of turns around said second mandrels has a different cross sectional area.

10. The device of claim 1, wherein the second number of turns of the compensation coil are wound in a honeycomb pattern.

11. The device of claim 1 wherein said first and second mandrels are made of a nonmagnetic material.

* * * * *